(12) United States Patent
Nauts et al.

(10) Patent No.: US 12,102,772 B2
(45) Date of Patent: Oct. 1, 2024

(54) ADAPTIVE ENTERTAINMENT CONTENT LENGTH DURING MEDICAL PROCEDURES

(71) Applicant: KONINKLIJKE PHILIPS N.V., Eindhoven (NL)

(72) Inventors: Sanne Nauts, Eindhoven (NL); Edwin Heijman, Eindhoven (NL); Annerieke Heuvelink-Marck, Eindhoven (NL); Doortje Van de Wouw, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 18/286,380

(22) PCT Filed: Apr. 8, 2022

(86) PCT No.: PCT/EP2022/059458
§ 371 (c)(1),
(2) Date: Oct. 11, 2023

(87) PCT Pub. No.: WO2022/223323
PCT Pub. Date: Oct. 27, 2022

(65) Prior Publication Data
US 2024/0091488 A1    Mar. 21, 2024

(30) Foreign Application Priority Data

Apr. 20, 2021 (NL) .................................... 2028016

(51) Int. Cl.
*A61M 21/02* (2006.01)
*A61B 5/055* (2006.01)
(Continued)

(52) U.S. Cl.
CPC ........ *A61M 21/02* (2013.01); *H04N 21/2143* (2013.01); *H04N 21/472* (2013.01);
(Continued)

(58) Field of Classification Search
CPC .......... A61M 21/02; A61M 2021/0027; A61M 2021/005; H04N 21/2143; H04N 21/472
See application file for complete search history.

(56) References Cited

U.S. PATENT DOCUMENTS

2007/0199023 A1\* 8/2007 Small ..................... H04N 7/163
725/74
2013/0245364 A1    9/2013 Gillies et al.
(Continued)

FOREIGN PATENT DOCUMENTS

WO        2015044128 A1      4/2015
WO    WO-2018209275 A1 \*  11/2018
WO        2020157056         6/2020

OTHER PUBLICATIONS

International Search Report and Written Opinion from PCT/EP2022/059458 mailed Jul. 11, 2022.
(Continued)

*Primary Examiner* — Thaddeus B Cox
*Assistant Examiner* — Joshua Daryl D Lannu

(57) ABSTRACT

Entertainment provided to a patient during a conscious medical procedure is adaptively created and updated such that the length of the entertainment matches the length of the medical procedure even if the length of the medical procedure is extended or shortened while it is ongoing.

18 Claims, 6 Drawing Sheets

(51) Int. Cl.
  *A61B 5/16* (2006.01)
  *A61M 21/00* (2006.01)
  *G16H 20/40* (2018.01)
  *G16H 20/70* (2018.01)
  *G16H 30/20* (2018.01)
  *H04N 21/214* (2011.01)
  *H04N 21/472* (2011.01)

(52) U.S. Cl.
  CPC .............. *A61M 2021/0027* (2013.01); *A61M 2021/005* (2013.01)

(56) References Cited

U.S. PATENT DOCUMENTS

| | | |
|---|---|---|
| 2014/0055133 A1 | 2/2014 | I et al. |
| 2015/0297148 A1 | 10/2015 | Biber et al. |
| 2016/0234486 A1 | 8/2016 | Klaming et al. |

OTHER PUBLICATIONS

Mirza-Babaei Pejman et al: "A Universe Inside the MRI Scanner: An In-Bore Virtual Reality Game for Children to Reduce Anxiety and Stress", Proceedings of The Annual Symposium on Computer-Human Interaction in Play Nov. 2, 2020 (Nov. 2, 2022), pp. 46-57.

* cited by examiner

ADAPTIVE ENTERTAINMENT CONTENT LENGTH DURING MEDICAL PROCEDURES

CROSS REFERENCE TO RELATED APPLICATIONS

This application is a U.S. national phase application of International Application No. PCT/EP2022/059458 filed on Apr. 8, 2022, which claims the benefit of NL Application Serial No. 2028016 filed on Apr. 20, 2021 and is incorporated herein by reference.

FIELD OF THE INVENTION

The present invention generally relates to an adaptive entertainment provider and a corresponding method and computer program.

BACKGROUND OF THE INVENTION

To reduce patient's anxiety and improve their experience during a conscious medical diagnostic or therapeutic procedure, such as, for instance a Magnetic Resonance Imaging (MRI) scan, patients may be supplied with entertainment content, such as a movie, during the procedure. For example, during MRI procedures, an in-bore entertainment screen or MRI-compatible movie goggles may be used to display a movie to the patient during the procedure.
Alternatively, audio content, such as music, soundscapes or stories, may be provided to the patient using, for instance, headphones. Audio and video may also be combined or even augmented with interactive content (i.e. games and the like). Further, video and/or audio content may also relate to patient instructions (e.g. a motion guide, a breathing guide, remaining procedure length, warnings, etc.) which may be integrated and/or alternated with the entertainment media.

US 2007/199023 discloses an entertainment sequence to reduce anxiety of a patient undergoing a medical procedure in which the entertainment sequence is matched to the medical procedure.

A problem with known entertainment content providers for use during a medical procedure is that the provided entertainment is often not of the same duration as the medical procedure, yielding a suboptimal experience for patients. Whenever a movie or audio content is shorter than the medical procedure (e.g. an MRI examination takes 20 minutes and the movie takes only 12 minutes), additional content (e.g. a new movie) has to be started by the physician, operator or assistant, which: takes time and could disrupt the workflow; could lead to a suboptimal patient experience, the patient may think the procedure is finished, and/or cause patient motion, which may be detrimental to the result of the procedure (e.g. blurred scan images causing the need for a rescan or, in extreme cases, missing a medical target in a therapeutic or surgical procedure).

Whenever the entertainment is longer than the full medical procedure (e.g. a diagnostic scan takes 3 minutes and the supplied movie has still 4 minutes to go), the patient cannot finish it, which also may lead to a suboptimal experience for patients and, in the case of pediatric patients, workflow disruptions (e.g. when pediatric patients do not want to leave the scanner while they are in the middle of an exciting movie).

Liszio et. al disclose, in "A Universe Inside the MRI Scanner: An In-Bore Virtual Reality Game for Children to Reduce Anxiety and Stress' Proc. Ann. Symp. on Computer Interaction in Play, p. 46-47 (2020), a virtual reality game that is optimally matched to the length of a medical procedure by programming the game runtime to suit the typical procedure length.

Creating such entertainment content with the right duration is difficult, in part because the length of the procedure may change over the course of the procedure, for instance because MRI sequences are added to an MRI scan, e.g. in case a rescan is requested by the MRI technologist. As artificial intelligence algorithms are maturing fast, scan quality monitoring during scanning is maturing as well and scan errors may be detected even earlier and more regularly. Therefore rescans or adaptive scans will become more common. Thus, the required duration of the movie is not always known before the entertainment content is started; while it is playing (and the medical procedure is in progress), it has to be continuously updated based on new estimates of the duration of the medical procedure.

One known way to deal with this issue is by presenting patients with entertainment content that does not contain a narrative or storyline (e.g. a landscape, dolphins swimming in the sea, nature sounds, etc.). Such a short movie or audio content is often put on a loop and patients see it multiple times if their scan takes long, or several unrelated movies or audio files are joined together (e.g. starting with a movie clip of swimming dolphins; switching to a movie clip of a desert landscape, etc.) and played until the scan is finished.

Unfortunately, this solution is not optimally entertaining and/or immersive. It is known that immersive content, such as engaging and/or narrative movie plots or audio content, results in an increased patient experience, less motion and therefore increased results and an improved workflow. In general, non-narrative storylines (e.g. seeing a swimming dolphin) may be less immersive than narrative storylines, as patients may get bored, disinterested, distracted or even annoyed by seeing or hearing very basic and/or the same content.

Therefore, it would be advantageous if immersive entertainment content could always be matched to the length of the medical procedure, even if the procedure changes while it is being performed.

SUMMARY OF THE INVENTION

Embodiments according to the present invention are directed to an adaptive entertainment content provider and a corresponding method and computer program for providing an entertainment sequence to a patient during a medical procedure with an initial procedure length. The content provider comprises an entertainment content database which comprises entertainment options. Each entertainment option includes at least one fixed content block, wherein each of the at least one fixed content blocks contains a section of entertainment content that was determined to be essential to provide a coherent entertainment sequence and includes metadata relating to the length of the fixed content block, and at least one optional content block, wherein each of the at least one optional content blocks contains a section of entertainment that was determined to be non-essential to provide a coherent entertainment sequence and includes metadata relating to the length of the optional content block. The content provider further comprises an initial content provider that is configured to create an initial entertainment sequence with an initial entertainment sequence length corresponding to the initial procedure length. This creation is achieved by selecting all of the least one fixed content blocks from the entertainment content database, and determining, from the data relating to the length of the fixed content blocks, the fixed entertainment sequence length and comparing the fixed entertainment sequence length with the initial procedure length. In case the fixed entertainment sequence length is less than the initial procedure length, the remaining content length to be filled is determined and then further selecting one or more of the at least one optional content blocks using the metadata relating to the length of the optional content blocks such that all of the selected at least one optional content blocks have a combined length matching the remaining content length. The content provider further comprises an updated content provider configured to receive an updated procedure length when the procedure length is changed during the procedure, and update the entertainment sequence by adding, from the entertainment content database, or removing, from the entertainment sequence, at least one optional content block using the metadata relating to the length of the optional content blocks such that the updated entertainment content has a length matching the changed procedure content length. The content provider further comprises an entertainment sequence provider configured to provide the entertainment sequence to the patient.

As such entertainment content may be provided to the patient with a length that matches the medical procedure length and in case something changes during the procedure that cause an increase or decrease of the procedural length, the entertainment length is adapted to match the updated procedure length by inserting or removing optional entertainment content blocks. The patient therefore always has a full entertainment sequence without a significant time wherein there is no entertainment or wherein the entertainment is not yet finished. This enhances the patient experience and reduces patient motion or workflow disruptions.

In an embodiment the entertainment sequence comprises visual entertainment, such as a movie, a sequence of photographs, (interactive) game scenes, virtual reality content or drawings and/or a text, and/or auditory entertainment, such as music, spoken word an/or ambient sounds. The presently claimed invention is suitable for all mentioned types of entertainment and more to optimally suit the patient's preferences as long as it is not limited by requirements of the actual medical procedure (e.g. games may not be possible if patient motion is undesirable).

In an embodiment the medical procedure is a diagnostic scan, such as a magnetic resonance scan, a computed tomography scan, a positron emission tomography scan, a single-photon emission computed tomography scan an ultrasound scan, fluoroscopy; or a surgical or therapeutic procedure wherein the patient is conscious, such as a biopsy, catheterization, minimally) invasive surgery, image-guided treatment or therapy, radiotherapy, proton therapy, infusion of a medication or contrast agent, dialysis. These are medical procedures wherein the patient is usually conscious and only locally or mildly sedated and the presently claimed invention is therefore particularly suitable as the patient's own experience and voluntary or involuntary response thereto may influence the outcome of the medical procedure. As such, influencing the patient's experience positively will likely result in better results for the medical procedure.

In an embodiment each of the at least one optional content blocks comprises further metadata relating to prioritization and/or constraints relating to the use of the optional data block. The updated content provider is configured to add or remove the at least one optional content block using the metadata relating to length and the further metadata relating to prioritization and/or constraints. As such the provided entertainment may be updated by adding or removing the most suitable or appropriate optional content block, as some optional content blocks may be more interesting to the narrative or better positioned to add or remove.

In an embodiment the content provider further comprises a user input configured to receive user input relating to the initial procedure length, updated procedure length, preferred entertainment option, patient information. The initial content provider and/or the updated content provider are configured to use the user input to respectively select or update the initial entertainment sequence. As such the user may select the most optimal entertainment option for the patient, which adds to making sure that the patient's experience is as pleasant and suitable as possible, which likely result sin better results of the medical procedure.

In an embodiment the updated content provider is further configured to adapt the length of the at least one fixed content blocks and/or at least one optional blocks. This allows for fine-tuning the length of the complete entertainment sequence more precisely if no optional content blocks are available that match the desired length to be added or removed.

In an embodiment the updated content provider is configured to adapt the length of the at least one fixed content blocks and/or at least one optional blocks by removing at least one sub-section of a content block, preferably at least one pre-determined sub-section that was previously determined to be less essential to provide a coherent entertainment sequence and preferably the metadata of the content block comprised at least one sub-section start and end point and optionally further metadata relating to prioritization and/or constraints. This in effect creates sub-sections of content blocks that may be cut to adapt a desired length of the content block. This sub-division may be handled similar to the difference between fixed and optional content blocks by determining the value of the sub-section to the narrative.

In an embodiment the updated content provider is configured to adapt the length of the at least one fixed content blocks and/or at least one optional blocks by changing the playback speed of a content block, preferably in cases when the length of the content block needs to be adapted with 30 seconds or less and preferably the content blocks contains metadata relating to the suitability of the block to have its speed changed and optionally with how much the length of the content block can be changed. As such a content block length may be extended or shortened somewhat to obtain a length that more closely matches the desired remaining content length. This is particularly suitable in case where the content block duration needs to be changed only with relatively small lengths and/or with content blocks with repetitive or non-essential content.

In an embodiment the initial content provider is configured to provide an initial entertainment sequence that ends with an optional content block. This allows for more easily shortening the entertainment sequence, particularly late in the medical procedure, while still supplying a satisfying narrative and/or ending.

In an embodiment the initial content provider and/or the updated content provider are configured to add and/or remove optional entertainment content blocks using a constraint satisfaction problem model. This is a particularly suitable model that can be implemented in the decision which blocks to add or remove.

In an embodiment the initial content provider and/or the updated content provider are configured to provide a smooth transition between two consecutive content blocks in the entertainment sequence, for instance by (cross-)fading. This allows for a more natural and smooth experience for the patient in which he does not notice that blocks are added or removed before or during the medical procedure.

In an embodiment the initial procedure length includes a pre-procedural length, which is defined as the time between the start of the entertainment and the start of the medical procedure. This allows to already start the entertainment in the period before the medical procedure, i.e. waiting time or preparation time, which helps to reduce anxiety, boredom and the like before the procedure as well and to provide a more immersive and homogeneous experience. All these factors will help in making the patient's experience more pleasant and the quality and likelihood of a successful medical procedure greater.

Still further aspects and embodiments of the present invention will be appreciated by those of ordinary skill in the art upon reading and understanding the following detailed description. Numerous additional advantages and benefits will become apparent to those of ordinary skill in the art upon reading the following detailed description of preferred embodiments.

DETAILED DESCRIPTION OF EMBODIMENTS

Figure 1:
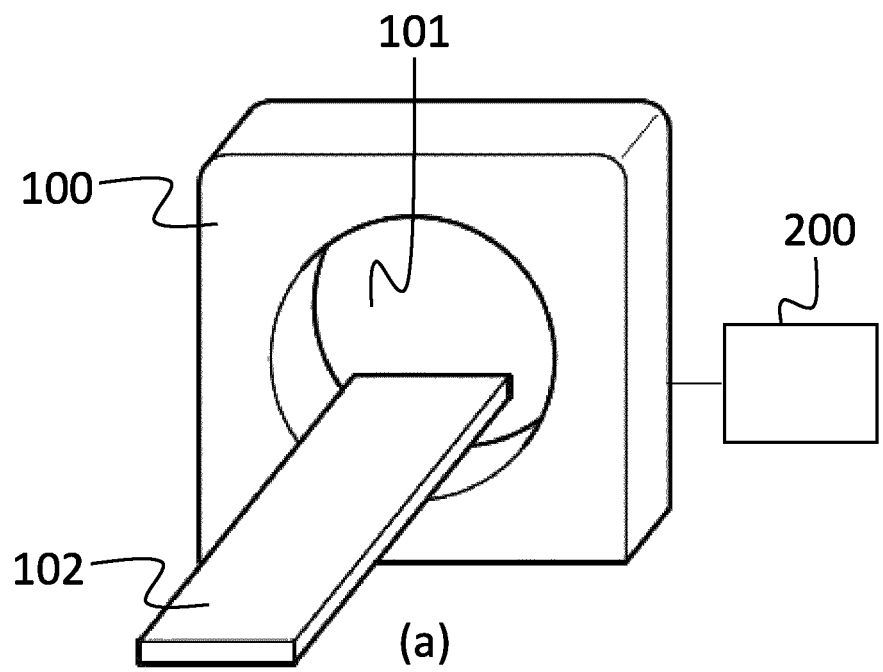
FIG. 1 shows a schematic depiction of an imaging device and a photograph of an exemplary in-bore entertainment provider.
Figure 1:
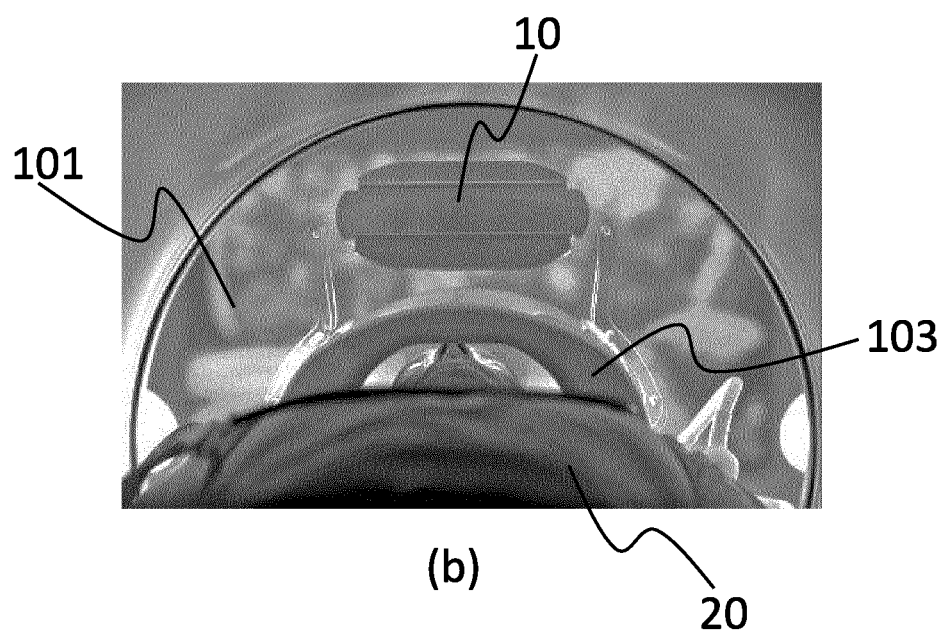

The presently claimed invention will be described using in-bore video entertainment during an magnetic resonance imaging (MRI) scan as an example, but is certainly not limited to this or even one type of MRI procedure. The presently claimed invention is suitable for many types of entertainment, including, but not limited to, movies and other visual entertainment, such as a sequence of photographs or drawings or a text, virtual reality imagery, (click-through) games, and/or auditory entertainment, such as music, spoken word (e.g. an audiobook), or ambient sounds. The presently claimed invention is suitable for all medical procedures wherein the patient is conscious during all or part of the procedure (e.g. with no, local or delayed anaestiasia), such as diagnostic imaging procedures, such as MRI, x-ray, computed tomograph, ultrasound, positron emission spectroscopy, single-photon emission computed tomography, fluoroscopy and the like; a surgical or therapeutic procedure, such as a biopsy, catheterization, (minimally) invasive surgery, image-guided treatment or therapy, radiotherapy, proton therapy, infusion of medication or contrast agent, dialysis and the like.

In an MRI device 100 a patient 20 on a patient support 102 is placed in the bore 101 of the MRI device 100, which uses strong magnetic fields, magnetic field gradients and radio waves (picked up by receiving coils 103) and a processing unit 200 to generate images of the organs in the patient's body. A schematic set-up is shown in FIG. 1a and photograph of a patient 20 inside a bore 101 is shown in FIG. 1b.

As is immediately clear from FIG. 1b, the bore 101 is relatively small and the head coil 103 is placed closely over the patient's head, creating a very narrow space that may induce claustrophobic feelings in the patient. Furthermore, the MRI scan may take between a few minutes to even an hour an half or more in which the patient has to lie still, while the procedure involves regular and irregular loud noises close to the patient's ears. All these factors contribute to the patient feeling uncomfortable, claustrophobic, impatient or even scared. This is particularly relevant for pediatric or psychiatric patients. To provide distraction and relief an in-bore entertainment system 10 that provides entertainment to the patient during the scan may be used. The entertainment system may for instance be in in-bore display or a mirror or screen onto which the entertainment content is projected. The entertainment system 10 usually includes headphones (not shown), which also reduce ambient noises and may be used to communicate with the patient 20. The entertainment system 10 may also include means for providing visual information and entertainment, such as an (MRI-compatible) in-bore screen, a screen placed outside of the bore that is seen through a mirror (as shown in FIG. 1b), a screen on the ceiling of the imaging room, 2D or 3D (MRI-compatible) (virtual reality) goggles, a projected screen and the like, which again also may be used to provide the patient with instructions and/or information relating to the scan (e.g. time left, a scan progress bar) as well as entertainment.

As mentioned in the background section of this document, it may be problematic when the length of the entertainment is not immersive and/or has is not of the same length as the length of the procedure, which may actually contribute to a poor patient experience and the risk of sub-optimal or even non-usable scan results causing a rescan or even a misdiagnosis. While many procedures may be planned and performed according to plan (which may be followed using an ExamCard that includes all the relevant and necessary scan data), it may occur regularly that during the scan the plan is adapted and the ExamCard is updated. For instance, a running procedure may be lengthened because a (partial) rescan may need to be done in case of patient movement or another irregularity or an additional scan may be planned if during the procedure additional information is obtained from the ongoing scan(s). Alternatively, an ongoing procedure may be shortened, for instance when a patient needs additional instructions during the scan that may pause the entertainment (thereby shortening the remaining time to provide the entertainment) or a planned follow-up scan may be cancelled due to additional information obtained from the ongoing scan(s).

The presently claimed invention provides an adaptive, preferably immersive, entertainment content provider that ensures that the length of the provided entertainment matches the procedure length, even if the procedure length is either lengthened or shortened during the medical procedure, and as such makes the patient's experience to be more satisfying, calming and/or bearable. This directly results in increased image quality, as movement is likely to be much less. This results in lower change of misdiagnoses and/or fewer procedures that need to be aborted and restarted due to disruptions caused by a patient's adverse mental state (e.g. anxiety, boredom, annoyance or any other negative mental state that may cause movement).

It is an insight underlying the presently claimed invention that most entertainment has a sequence of entertainment sections with some sections that are essential to tell a story or provide a full experience and other sections that are not essential to the central plot, but do enrich the story by providing more context, side-stories and/or deepen character characteristics. As such a full entertainment sequence may be sub-divided into several sections, hereafter called blocks in the context of this invention, and each block may be flagged as being essential (fixed content blocks) or are not essential (optional content blocks). In its most basic embodiment, the provided entertainment content may built up using all fixed content blocks, and if the planned procedure is longer than the time of the fixed content blocks, then optional content blocks may be added among the fixed content blocks.

Figure 2:
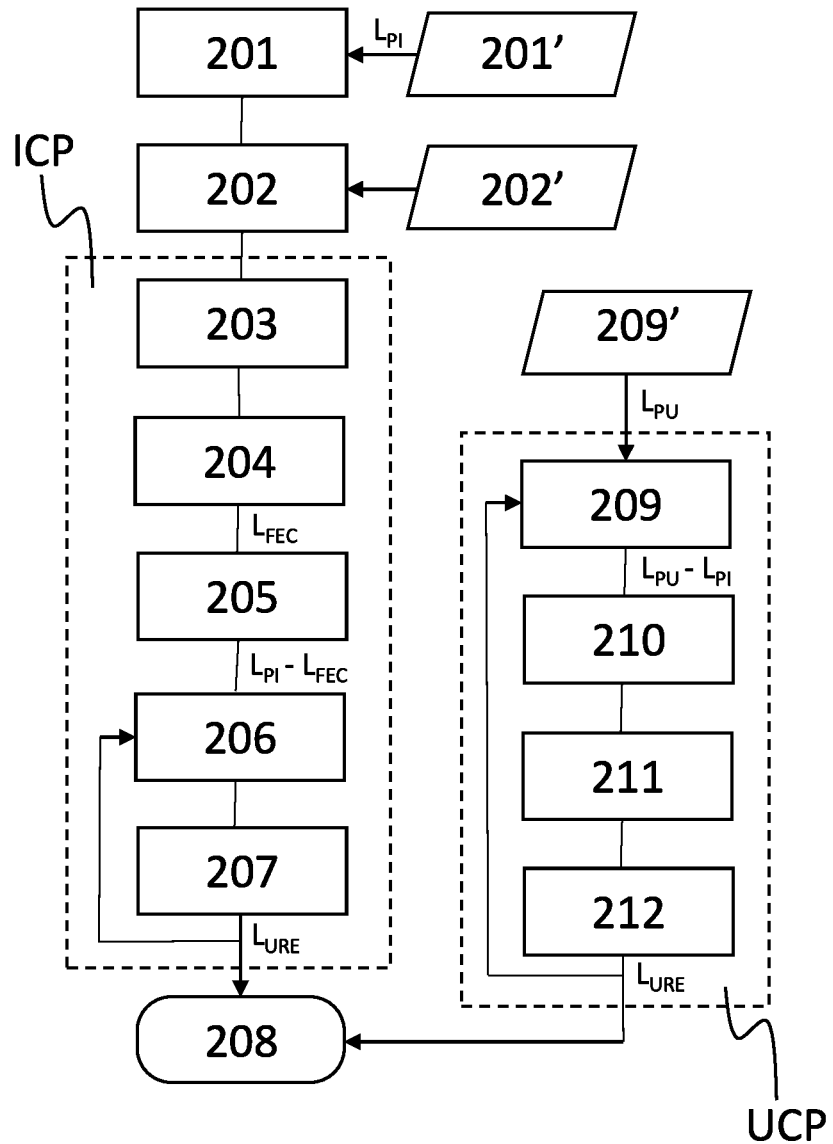
FIG. 2 shows an exemplary workflow of a method to provide adaptive entertainment according to the presently claimed invention.

FIG. 2 shows an exemplary flowchart of basic method steps relating to an embodiment according to the presently claimed invention.

First (step 201), an initial procedure length ($L_{IP}$) is determined based on the ExamCard or any other planning method. This is usually provided (step 201') manually by the physician or technologist responsible for the scan, but it may also be performed (semi)-automatically by a processor that calculates the initial procedure length from received procedural input.

Next (step 202), an entertainment option is chosen (step 202') by the patient and/or operator from an entertainment database, for instance using a fixed or remote screen showing entertainment categories or topics. The entertainment base may be an on-site or cloud-based server from which content is downloaded or streamed to the entertainment system. Preferably only options are shown for which the total time of fixed blocks is the same or smaller than the initial procedure time.

Preferably, the shown entertainment options are further preselected based on patient characteristics, such as age or sex. To facilitate this process, several categories are preferably provided, e.g. short, middle and long movies with an entertainment base (all, but just the fixed content blocks) of, e.g. respective 10, 30 and 50 minutes. In addition, a possible movie theme or target group (e.g. 'adults' or 'children 4-10') may be selected. The selected entertainment base, which should be shorter than or have the same length as the expected procedure length, is then extended to the desired duration by selecting content blocks from the pool of possible optional content blocks. To leave as much flexibility as possible to the chance of a procedure being shortened, it is preferably ensured that an optional block is added to the end and that there is a good spread of optional content blocks across the entertainment sequence.

Each entertainment option (e.g. a single movie) comprises at least one (but preferably at least two or more) fixed content block (F-1, F-2, F-3, ... ) and at least one (but preferably a multitude of) optional content blocks (O-1, O-2, O-3, ... ). Each content block has a specified length, which is stored in metadata of the content block. The entertainment options may be existing visual or auditory entertainment or may be specifically created for this purpose. Whether a content block is essential or non-essential to the storyline was previously determined, preferably by an expert on storytelling or may be determined using machine learning or artificial intelligence algorithms.

Next (step 203), an initial content provider (ICP), preferably implemented as a program running on an on-site or cloud-based processor, selects and sequences all fixed entertainment blocks (F-1, F-2, F-3, ... ) of the selected entertainment option to build a fixed entertainment sequence (entertainment base).

The initial content provider then calculates (step 204) the length of the fixed entertainment sequence using the metadata related to the block length for each content block by adding the lengths of the selected fixed entertainment blocks to obtain the fixed entertainment content length ($L_{FEC}$).

Next (step 205), the initial content provider determines a difference between the fixed entertainment content length and the procedure length to obtain a remaining entertainment sequence length ($L_{PI}-L_{FEC}$).

Next (step 206), the initial content provider selects from the at least one available and suitable optional content blocks, using the metadata related to the length of each of the at least one optional content block, an optional content block with a length that corresponds as closely as possible with the remaining entertainment sequence length. If no optional content block is available with the correct length then an optional content block is selected that has a length that is shorter than the remaining entertainment sequence length.

Next (step 207), an updated remaining entertainment length (LURE) is then calculated by the initial content provider. In case the updated entertainment length is still shorter than the initial procedure length, then this step is repeated to select one or more blocks until the initial procedure length is reached and an initial entertainment content sequence is obtained. If no optional content blocks are available of the correct length then the content provider may redo step 206 and select a different optional content block first and then add another optional content block or blocks with which the combined length does match the remaining entertainment sequence length.

In practice it is acceptable if the entertainment length is not exactly, 'on the second' the same as the procedure length and a few (less than 5 seconds, less than 10 seconds, less than 20 seconds) may be acceptable, depending on the procedure and the patient. For instance, a few remaining seconds is usually not difficult to wait for and there is often a period between the end of the procedure and when the patient is taken away from his position he was in during the procedure, e.g. in MR imaging, when the procedure is finished it will always take 20-30 seconds for the technologist to open the door and slide the table out, given more than enough time to finish the last bit of the entertainment. Furthermore, the last bit of the movie might be a non-essential fade-out or credits scene. On the other hand if the entertainment length is slightly shorter than the procedure length, this will ensure that the patient is provided with closure of the entertainment (e.g. a narrative has come to an end). However it may cause motion and the like if it ends to early, which may be problematic if essential parts of the procedure take place in the final seconds of the procedure.

Next (step 208), the initial entertainment content sequence is played for the patient as soon as the medical procedure starts. This may be initiated automatically or manually. If no changes to the medical procedure length during the procedure occur, then the initial entertainment content sequence is played to the end, finishing at, substantially, the same time as the medical procedure.

In case the medical procedure length is shortened or lengthened during the procedure, for instance for reasons described previously, then (step 209) an updated content provider (UCP), preferably implemented as a program running on an on-site or cloud-based processor and, optionally, within the same program as the initial content provider, receives information (209'), automatically or manually, with an updated procedure length ($L_{UP}$) or information from which the updated content provider can calculate the updated procedure length.

Next (step 210), the updated content provider determines a difference between the initial procedure length and the updated procedure length ($L_{IP}$–$L_{UP}$).

Next (step 211), in case the initial procedure length is shorter than the updated procedure length (extended procedure), then the updated content provider selects one or more optional content blocks, in the same way as in steps 206 and 207. In case the initial procedure length is longer than the updated procedure length (shortened procedure), then the content updater selects one or more, as of yet unplayed, optional content blocks from the initial entertainment content sequence with a (combined) length that matches the determined difference between the initial procedure length and the updated procedure length and removes these from the initial entertainment content sequence. Preferably this occurs seamlessly such that the patient does not notice this.

Next (212), the resulting updated entertainment content sequence is provided to the patient until the end of the procedure or until the procedure length is again changed, in which case the updated content provider performs steps 209 to 211 again.

Preferably, in creating an initial or updated movie sequence the initial and/or updated content provider is configured to provide smooth transitions between any two consecutive content blocks, e.g. by fading or cross-fading between two content blocks.

Figure 3:
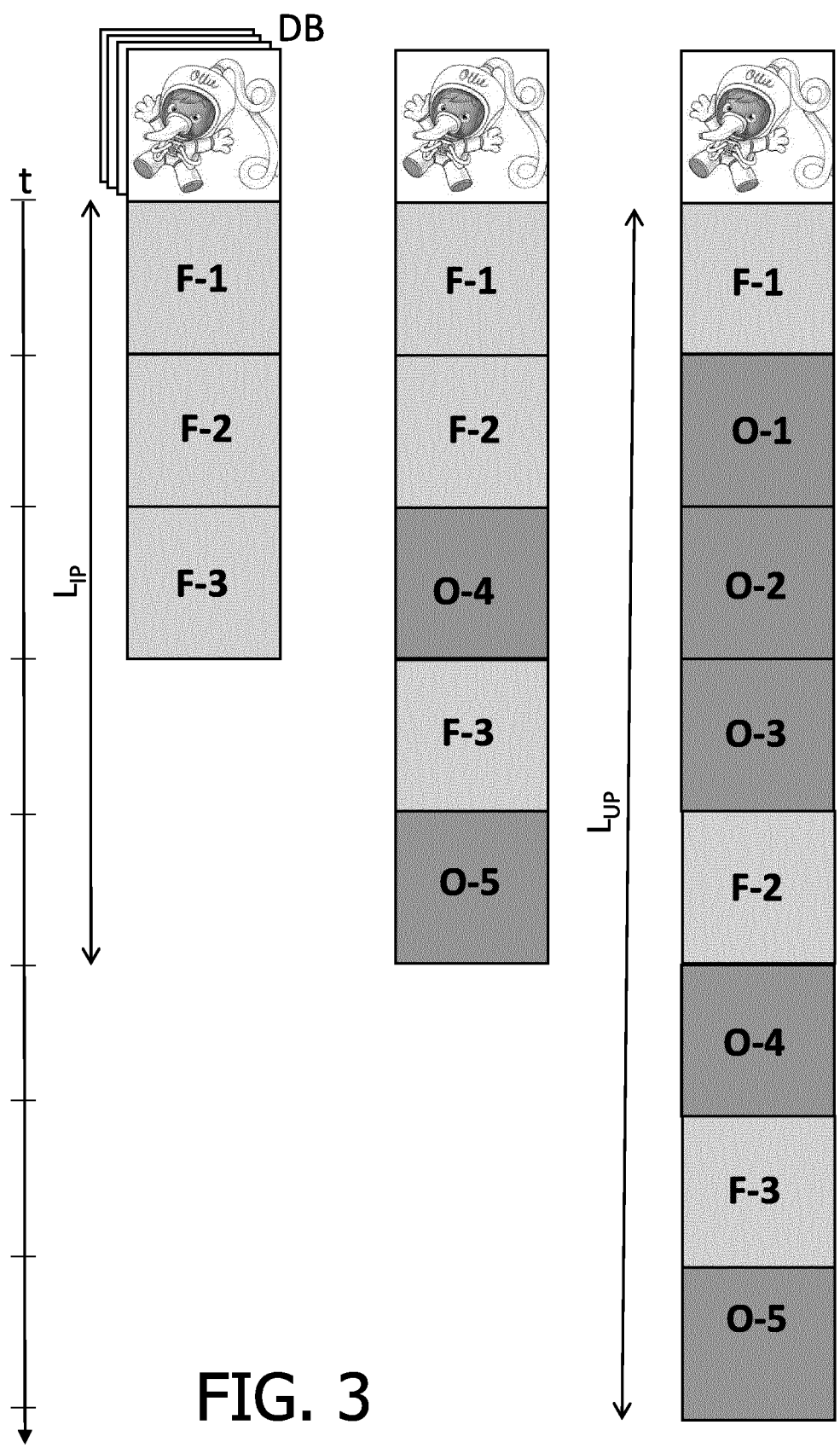
FIG. 3-6 show examples of different embodiments of adapting entertainment sequences according to the presently claimed invention The invention may take form in various components and arrangements of components, and in various process operations and arrangements of process operations. The drawings are only for the purpose of illustrating preferred embodiments and are not to be construed as limiting the invention. To better visualize certain features may be omitted or dimensions may be not be according to scale.

FIG. 3 depicts a schematic illustration of a non-limiting, explanatory situation in which the procedure length increases during the medical procedure. In this example the patient is a young child undergoing an MRI scan. The selected entertainment content from an entertainment database DB is a cartoon about an astronaut elephant that includes three fixed content blocks F-1, F-2, F-3 and a plurality of optional blocks O-1, O-2, O-3, O-4, O-5, . . . . In this example all content blocks are of the same length: 4 minutes per block.

The initial procedure length $L_{IP}$ is determined to be 20 minutes, which is provided as input to in a computer program that comprises an initial content provider. The combined length of the fixed block length (entertainment base) is 12 minutes. Therefore the remaining length is 8 minutes, which can be filled with two optional content blocks O-4, O-5 to obtain an initial movie sequence with a length that exactly matches the initial procedure length.

Early on during the MRI scan a decision is made to add another MRI sequence, which extends the procedure with 12 minutes to an updated procedure length of 32 minutes, which is provided as input to in the computer program that also comprises an updated content provider. As the first fixed block F-1 has not been fully played, the updated content provider can choose from all the available, as of yet unused optional content blocks and selects 3 optional content blocks O-1, O-2, O-3 that are placed in the movie sequence between the first and second fixed content blocks F-1, F-2. The updated movie sequence now matches the updated procedure length. In case the updated procedure time is determined later in the procedure less optional content blocks may become available as they would not make sense anymore in the storyline.

Figure 4:
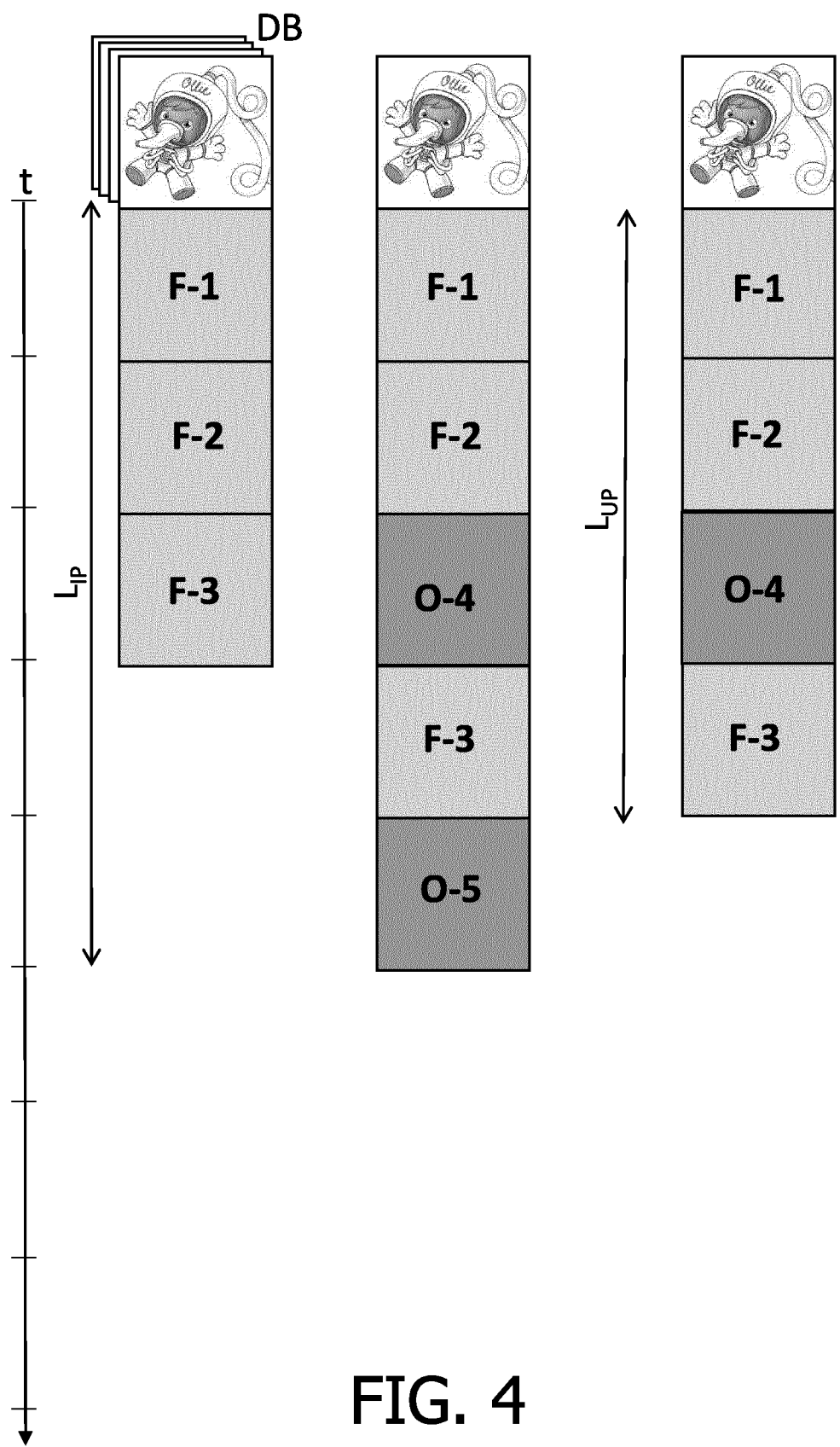

FIG. 4 depicts a schematic illustration of a similar non-limiting, explanatory situation, but in which the procedure length is shortened during the procedure. The same movie was selected, but in this example it was decided after 9 minutes into the procedure that the final part of the scan is not necessary, reducing the initial procedure length Lin with 4 minutes to an updated procedure length $L_{UP}$ of 16 minutes. As optional content block O-4 is already playing, the only option is to remove optional content block O-5 to arrive at a movie sequence with a length of 16 minutes. Even though optional block O-5 was placed at the end and was not essential to the main story, the content of such optional end content blocks is designed such that the patient receives a satisfying ending in addition to the ending of the main narrative (in fixed block F-3).

In more realistic embodiments the content blocks have varying lengths, e.g. 30 seconds, 1, 2, 3, 4, . . . minutes to allow for a more freedom to add content or to allow for many more initial or updated procedure lengths.

Figure 5:
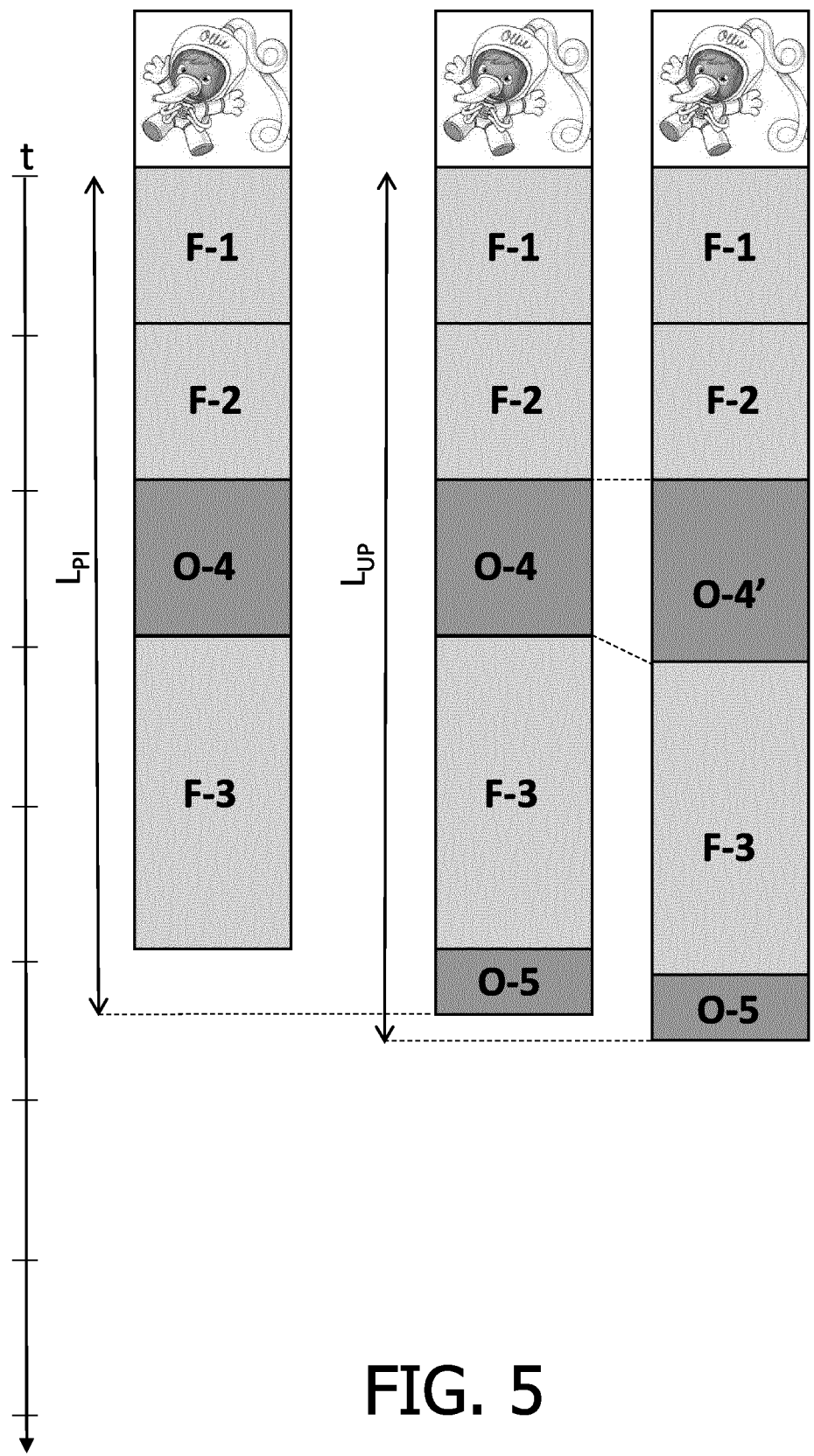

In FIG. 5 a non-limiting example is shown in which the initial procedure length is 18 minutes. In this case the sequence was built up to 16 minutes using three fixed content blocks F-1, F-2, F-3 and one optional content block O-4. A second optional content block O-5 is selected since it is 2 minutes long instead of 4 to fill out the remaining time to obtain a movie sequence matching the initial procedure length.

Preferably, the updated content provider is configured to change the length of the content blocks.

This may be achieved by either speeding up or slowing down the playback speed of the content block. This is particularly suitable in cases where there is only a small change in procedure length (e.g. less than 30 seconds, less than 20 seconds, less than 10 seconds, less than 5 seconds, less than 3 seconds or less than 1 second) and no blocks are available to add or remove that are short enough to match this change in length. Of course some content blocks may be more suitable than others, e.g. content blocks with some ambient images of landscapes or simple movement. If necessary the sound pitch may be corrected to account for the changed playback speed such that the patient does not notice anything. The speed of the fixed content blocks or and/or optional content blocks may be changed to obtain the updated movie sequence length.

In a second embodiment the updated content provider changes the length of a content block removing parts of a content block. In this case the content blocks must already have previously determined sub-sections that specify suitable sections that may be excised without loss of the narrative within the content block or the whole movie sequence, for instance sections without speaking or sections with no, repetitive or extended action. While it is more likely that such sections occur in optional content blocks, it may also be done in suitable fixed blocks.

FIG. 5 further depicts a variation of the same situation as described with FIG. 3, but in this case the updated procedure length is increased by 30 seconds. As all available optional content blocks are longer than this, the movie will end premature with optional content block O-5 or will not be finished if an added optional content block is added. In this example optional block O-4, which includes a short scene in which a rocket is launched into space with no dialogue and therefore is particularly suitable for this purpose, is slowed down to extend the content block length to 4 minutes and 30 seconds minutes. The sound of the block is automatically pitched to the right levels. The updated movie length now matches the updated procedure length and the patient would not notice that this scene was altered in any way. If the procedure would have been shortened instead, then the content block playback speed could be increased slightly (and pitch-corrected) to accommodate for the time reduction.

Figure 6:
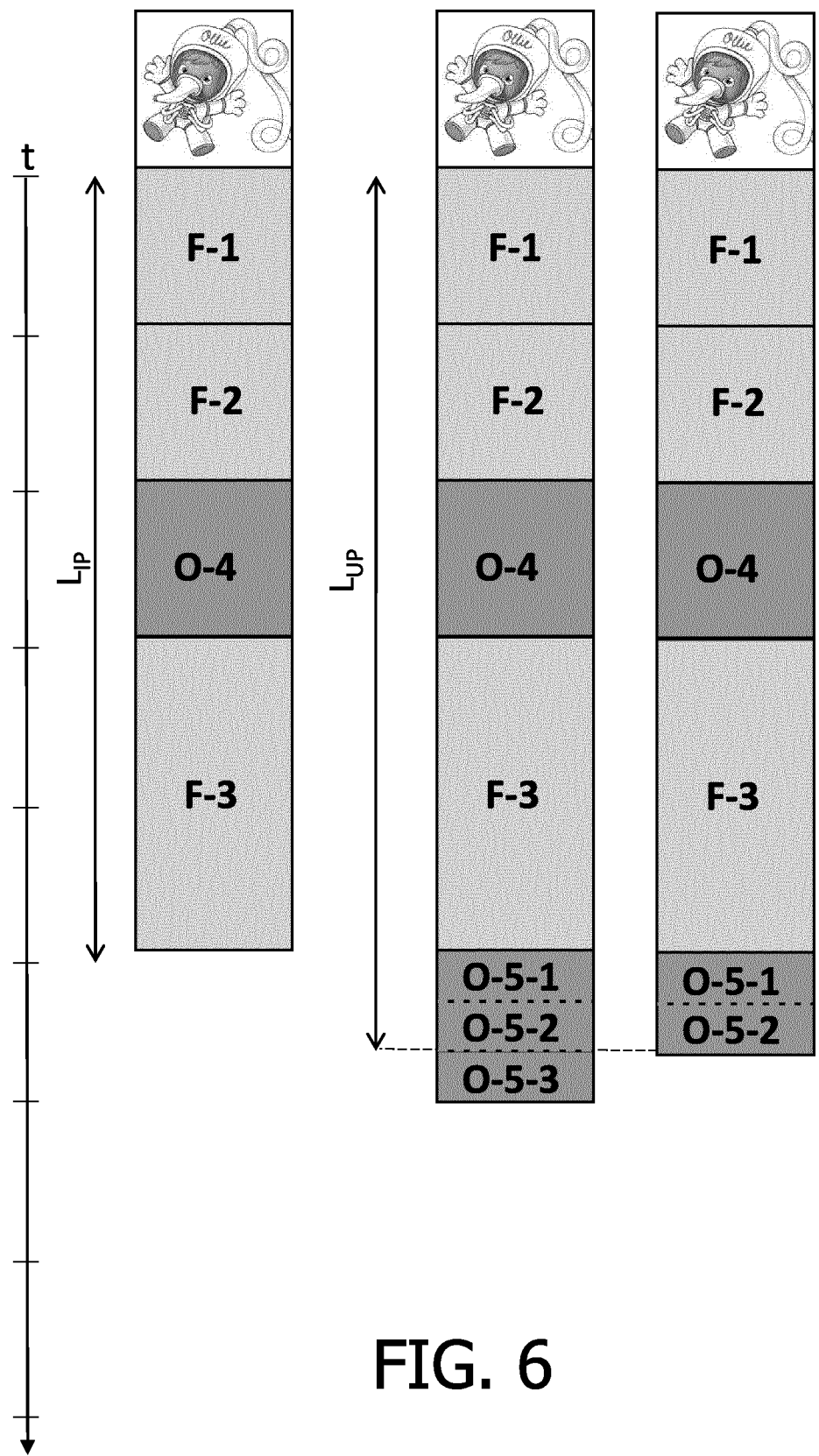

FIG. 6 depicts a similar situation as in FIG. 5, but now the procedure is extended by 3 minutes. No optional content block is available with the correct additional time, but the updated content provider recognizes that optional content block O-5 has been found to contain three sub-sections O-5-1 (2 minutes), O-5-2 (1 minute), O-5-3 (1 minute) (not drawn to scale in this figure) that are sub-scenes within the content block. The first and second sub-sections O-5-1, O-5-2 together have a length of 3 minutes. Therefore the updated content provider excises sub-section O-5-3 and only adds sub-sections O-5-1 and O-5-2 to the movie sequence, which now is exactly as long as the updated procedure length. Preferably, optional content blocks with such sub-sections contain metadata including sub-section start and end point and preferably prioritization and/or constraint information. Preferably, the updated content provider is configured to provide a smooth transition to the next sub-section or content block if one or more sub-sections of an optional block are removed.

The updated content provider may also perform combinations of the options to extend or shorten the movie sequence.

Preferably the metadata of the optional content block also comprises data relating to use constraints of the content optional content blocks O-3 and O-4 are 'unlocked' and can also be added to the storyline or when optional content block O-5 is played, optional blocks O-2, O-3 and O-4 are 'locked' and not available anymore.

Preferably the metadata of an optional content block also comprises data relating to prioritization of the content block. Some optional content blocks may have a greater added value to the main story than others and therefore may be chosen by the initial or updated content provider before an optional content block with a lower added value to the story. For instance, a priority score may be given to each optional content block, or sub-divisions within a content block, that may be accessed by the initial or updated content provider to choose the most suitable optional content block(s) to add to the entertainment sequence.

Table 1 shows an exemplary storyline for the story "Ollie goes to space" that is divided into three content fixed and eleven optional content blocks to form a movie sequence between seven minutes (the entertainment base of all fixed content blocks only) and twenty-two and a half minutes (all fixed and all optional content blocks).

TABLE 1

Storyline example.

| type | # | duration (min) | content |
|---|---|---|---|
| fixed | F-1 | 3 | Ollie is an astronaut. He wants to travel to the International Space Station (ISS) to conduct experiments to learn more about how plants grow in space. |
| optional | O-1 | 2 | Before Ollie goes to space, he first has to go to astronaut camp. There, he has to learn lots of things, like how astronauts live in space. |
| optional | O-2 | 1 | He also learns how to make repairs to equipment if it is broken. |
| optional | O-3 | 2 | He also learns how to deal with a lack of gravity! He learns this in a very cool, special buoyancy chamber, and also using VR goggles. |
| optional | O-4 | 3 | O no! Right before Ollie is set to go to space, something goes wrong with his science experiment! He does not have enough seeds to grow plants! Luckily, children from a nearby school help him, so he can go into space. |
| optional | O-5 | 1 | Ollie is now ready to go to space! He gets into his rocket, and there is a countdown! Now, he flies away. |
| optional | O-6 | 1 | Ollie sees all kinds of interesting things while he is in space e.g. Nebula. |
| optional | O-7 | 1 | Ollie sees all kinds of interesting things while he is in space e.g. Constellations. |
| fixed | F-2 | 2 | Ollie flies in his rocket and arrives at the ISS. He conducts his experiment and finds out that plants grow differently in space than on earth! |
| optional | O-8 | 2 | O no! Just when Ollie's experiment is done, something breaks down at the ISS and the astronauts have to fix it. Ollie goes out, makes the repair, and gets back into his rocket. |
| fixed | F-3 | 2 | Ollie goes back to earth, and everyone welcomes him home. Mission accomplished! |
| optional | O-9 | 1.5 | After landing, Ollie goes to a school to tell kids about what he learned from his space adventure, and all the kids love it! |
| optional | O-10 | 0.5 | Suzie now wants to be an astronaut, too, when she grows up. |
| optional | O-11 | 0.5 | Peter really loves plants and how they grow and would like to become a biologist, just like his mother. | block. For most optional content blocks the content relates to additional narrative or otherwise interesting content and in most cases they cannot be freely placed within the entertainment sequence. For instance, in the case of a cartoon of an elephant going to space an optional content block of the elephant floating in space cannot be placed before the rocket is launched or after he has returned to earth. Therefore, constraints of dependence on other content blocks may be added to the metadata, for instance before and/or after which content blocks a certain optional content block can be placed (e.g. when optional block O-2 is played, Table 2 shows an illustrative example of metadata for optional content blocks in the storyline 'Ollie goes to space' with constraints and prioritizations (a higher prioritization score means a more interesting addition to the storyline). In this example optional blocks that have a constraint that they have to follow another optional block (O-7 and O-6 or O-10 and O-11) can only be unlocked if the optional block that they need to follow itself was selected. Optional content blocks that have a constraint that they have to follow a fixed content block (e.g. O-1, O-2, O-3, O-4, O-5, O-8, O-9) can be freely chosen between the 'After' and 'Before' constraints. Preferably at least one optional content block is selected that has no 'Before' constraint, e.g. O-9, O-10 or O-11. Such blocks may be used as an end block in the sequence and are easy to remove in case the medical procedure is shortened even at a late stage.

TABLE 2

Optional block meta-information example

| Block | After | Before | Priority Score |
|-------|-------|--------|----------------|
| O-1   | F-1   | F-2, O-5 | 1 |
| O-2   | F-1   | F-2, O-5 | 2 |
| O-3   | F-1   | F-2, O-5 | 1 |
| O-4   | F-1   | F-2, O-5 | 3 |
| O-5   | F-1   | F-2   | 2 |
| O-6   | O-5   | F-2   | 2 |
| O-7   | O-5   | F-2   | 1 |
| O-8   | F-2   | F-3   | 3 |
| O-9   | F-3   | —     | 2 |
| O-10  | O-9   | —     | 2 |
| O-11  | O-9   | —     | 1 |

The presently claimed invention may be technically implemented using a constraint satisfaction problem (CSP), whereby Dynamic CSPs are particularly suitable.

A CSP is defined by 1) a set of variables; 2) a set of possible values (domain) for each variable; 3) constraints that restrict combinations of allowed values (relations between variables).

A constraint satisfaction problem is solved when there is a complete consistent instantiation of variables, also referred to as a solution. A solution is generally found by inference and search.

In the context of the presently claimed invention all the entertainment content blocks are considered to be variables. Values of the blocks can e.g. be 0 (absent in entertainment sequence), 1 (present, not played) or 2 (played). A unary constraint (involving a single variable) is e.g. that initially all fixed blocks receive the value 1. When the entertainment sequence needs to be adapted while it plays, a unary constraint is that all the played blocks (and currently active block) receive the value 2. Another unary constraint can be that the variable consisting of the durations of all the content blocks with the value 1 should be the duration of the remaining estimated scan time+0-30 seconds. Binary constraints (involving pairs of variables) may be used to check dependencies between content blocks. A general binary constraint that has to be instantiated and checked for each content block (for instance by using information similar to the example list in Table 2) is for example: Tor each Block(X) with X≠2, if Before(Y) and Y=2 then X=0'. When all the hard constraints are fulfilled by inference, the values of the remaining open variables can be filled by search.

Preferences (soft constraints), e.g. O-7 is more fun that O-6, can be explicitly represented by a cost for each variable assignment or implicitly by structuring the search in such a way that preferred options are found first.

A patient may already start enjoying entertainment while he is waiting for the procedure to start (e.g. while he is in an MR device while it is being set-up for the scan or even in a waiting room before entering the procedure room) and that may then, preferably seamlessly, be continued when the scan starts. The waiting time may also be included in the initial procedure length as a pre-procedural length, which is defined as the time between the start of the entertainment (e.g. as started by the physician or patient after selection) and the start of the actual procedure. As such, adaptive entertainment length may be introduced to also cover potential delays or shortening of the waiting time. While the problem of patient movement and adverse emotions (e.g. anxiety, boredom, anxiety etc.) while waiting does directly not result in potential complications during the procedure, it does increase the chance that the patient starts the procedure in a more relaxed state, with a higher chance of a successful procedure.

In a specific variation of the invention as claimed all content blocks may be optional content blocks and no fixed blocks are defined. In that case the selected optional block that starts the entertainment sequence is defined as a fixed content block in the context of the claimed invention.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

When in this document the term content block is used without the prefix fixed or optional, this usually indicates that it is relevant for both or it is clear from the context which type of content block is used.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An adaptive entertainment content provider configured to provide an entertainment sequence to a patient during a medical procedure with an initial procedure length, comprising:
   an entertainment content database (DB) comprising, for each of at least one entertainment option,
      at least one fixed content block, wherein each of the at least one fixed content blocks contains a section of entertainment content that was determined to be essential to provide a coherent entertainment sequence and includes metadata relating to a length of the at least one fixed content block, and
      at least one optional content block, wherein each of the at least one optional content blocks contains a section of entertainment that was determined to be non-essential to provide a coherent entertainment sequence and includes metadata relating to a length of the optional content block;
   an initial content provider (ICP) configured to create an initial entertainment sequence with an initial entertainment sequence length corresponding to the initial procedure length by:
      selecting all of the at least one fixed content blocks from the entertainment content database, and
      determining, from the metadata relating to the length of the at least one fixed content blocks, a fixed entertainment sequence length and comparing the fixed entertainment sequence length with the initial procedure length, and when the fixed entertainment sequence length is less than the initial procedure length, determining a remaining content length to be filled, and then further selecting one or more of the at least one optional content blocks using the metadata relating to the length of the at least one optional content blocks such that all of the selected at least one optional content blocks have a combined length matching the remaining content length;

an updated content provider (UCP) configured to:

receive an updated procedure length when the initial procedure length is changed during the procedure, and update the entertainment sequence by adding, from the entertainment content database, or removing, from the entertainment sequence, the at least one optional content block using the metadata relating to the length of the optional content blocks such that an updated entertainment content has a length matching the updated procedure length; and an entertainment sequence provider configured to provide the entertainment sequence to the patient.

2. The adaptive entertainment content provider according to claim 1, wherein the entertainment sequence comprises at least one selected from a group consisting of:

visual entertainment in a form selected from a visual entertainment group consisting of at least one of: a movie, a sequence of photographs, (interactive) game scenes, virtual reality content or drawings and/or a text; or auditory entertainment in a form selected from an auditory entertainment group consisting of at least one of music, a spoken word or ambient sounds.

3. The adaptive entertainment content provider according to claim 1, wherein the medical procedure is at least one selected from a group consisting of:

a diagnostic scan in a form selected from a diagnostic group consisting of: a magnetic resonance scan, a computed tomography scan, a positron emission tomography scan, a single-photon emission computed tomography scan an ultrasound scan, or a fluoroscopy scan; or a surgical or therapeutic procedure wherein the patient is conscious, wherein the surgical or therapeutic procedure is a biopsy, catheterization, minimally invasive surgery, image-guided treatment or therapy, radiotherapy, proton therapy, infusion of a medication or contrast agent, or dialysis.

4. The adaptive entertainment content provider according to claim 1, wherein each of the at least one optional content blocks comprises further metadata relating to prioritization and/or constraints relating to a use of the optional data block; and wherein the updated content provider is configured to add or remove the at least one optional content block using the metadata relating to length and the further metadata relating to prioritization and/or constraints.

5. The adaptive entertainment content provider according to claim 1, further comprising a user input configured to receive user input relating to the initial procedure length, updated procedure length, preferred entertainment option, patient information; and wherein the initial content provider and/or the updated content provider are configured to use the user input to respectively select or update the initial entertainment sequence.

6. The adaptive entertainment content provider according to claim 1, wherein the updated content provider is further configured to adapt the length of the at least one fixed content blocks and/or at least one optional content blocks.

7. The adaptive entertainment content provider according to claim 6, wherein the updated content provider is configured to adapt the length of the at least one fixed content blocks and/or at least one optional content blocks by removing at least one sub-section of the content blocks or the least one optional content blocks.

8. The adaptive entertainment content provider according to claim 6, wherein the updated content provider is configured to adapt the length of the at least one fixed content blocks and/or at least one optional content blocks by changing a playback speed of at least one of the fixed content blocks or the at least one optional content blocks.

9. The adaptive entertainment content provider according to claim 6, wherein at least one pre-determined sub-section of the at least one fixed content blocks and/or at least one optional content block that was previously determined to be less essential to provide a coherent entertainment sequence includes metadata relating to the prioritization and/or constraints.

10. The adaptive entertainment content provider according to claim 6, wherein the metadata of the at least one optional content block includes at least one sub-section start and end point.

11. The adaptive entertainment content provider according to claim 10, wherein the metadata includes information relating to prioritization and/or constraints of the at least one optional content block.

12. The adaptive entertainment content provider according to claim 6, wherein when the length of the content block needs to be adapted by 30 seconds or less, the content blocks contain metadata relating to suitability of the block to have its speed and/or length changed.

13. The adaptive entertainment content provider according to claim 1, wherein the initial content provider is configured to provide the initial entertainment sequence that ends with an optional content block.

14. The adaptive entertainment content provider according to claim 1, wherein the initial content provider and/or the updated content provider are configured to add and/or remove optional content blocks using a constraint satisfaction problem (CSP) model.

15. The adaptive entertainment content provider according to claim 1, wherein the initial content provider and/or the updated content provider are configured to provide a smooth transition between two consecutive content blocks in the entertainment sequence.

16. The adaptive entertainment content provider according to claim 1, wherein the initial procedure length includes a pre-procedural length, which is defined as a time between a start of the entertainment and a start of the medical procedure.

17. A method to adaptively provide an entertainment sequence to a patient during a medical procedure with an initial procedure length, comprising:

selecting an entertainment option from an entertainment content database comprising, for each of at least one entertainment option, at least one fixed content block, wherein each of the at least one fixed content blocks contains a section of entertainment content that was determined to be essential to provide a coherent entertainment sequence and includes metadata relating to a length of the fixed content block, and at least one optional content block, wherein each of the at least one optional content blocks contains a section of entertainment that was determined to be non-essential to provide a coherent entertainment sequence and includes metadata relating to a length of the optional content block;

creating an initial entertainment sequence with an initial entertainment sequence length corresponding to the initial procedure length by:

selecting all of the at least one fixed content blocks from the entertainment content database, and determining, from the metadata relating to the length of the at least one fixed content blocks, a fixed entertainment sequence length and comparing the fixed entertainment sequence length with the initial procedure length, determining a remaining content length to be filled based on the comparison of the fixed entertainment sequence length with the initial procedure length, and further selecting, zero, one, or more of the at least one optional content blocks using the metadata relating to the length of the at least one optional content blocks such that all of the selected at least one optional content blocks have a combined length matching the remaining content length;

receiving an updated procedure length when the initial procedure length is changed during the procedure, and updating the entertainment sequence by adding, from the entertainment content database, or removing, from the entertainment sequence, the at least one optional content block using the metadata relating to the length of the optional content blocks such that the updated entertainment content has a length matching the updated procedure length; and providing the entertainment sequence to the patient.

18. A computer program product comprising executable instructions stored on a non-transitory computer readable medium, which when run on a processor, performs the steps of the method of claim 17, wherein the selecting of an entertainment option from an entertainment content database may be a direct response from a user input.

* * * * *